(12) United States Patent
Bittmann et al.

(10) Patent No.: US 6,582,471 B1
(45) Date of Patent: Jun. 24, 2003

(54) COMPOSITION AND DEVICE FOR IN VIVO CARTILAGE REPAIR

(75) Inventors: Pedro Bittmann, Zürich (CH); Brent Atkinson, Lakewood, CO (US); James J. Benedict, Golden, CO (US); John Ranieri, Austin, TX (US); Marsha L. Whitney, Austin, TX (US); Donald Chickering, Framingham, MA (US)

(73) Assignee: Sulzer Innotec AG, Winterthur (CH)

( * ) Notice: Subject to any disclaimer, the term of this patent is extended or adjusted under 35 U.S.C. 154(b) by 0 days.

(21) Appl. No.: 09/485,594

(22) PCT Filed: Aug. 12, 1998

(86) PCT No.: PCT/EP98/05100
§ 371 (c)(1),
(2), (4) Date: Sep. 13, 2000

(87) PCT Pub. No.: WO99/08728
PCT Pub. Date: Feb. 25, 2000

(30) Foreign Application Priority Data

Aug. 14, 1997 (EP) ............................................. 97810567

(51) Int. Cl.$^7$ .................................................. A61F 2/36
(52) U.S. Cl. .................................. 623/23.63; 623/23.51
(58) Field of Search ............................. 623/13.11, 13.12, 623/13.17, 13.18, 23.51, 23.61, 23.62, 23.63

(56) References Cited

U.S. PATENT DOCUMENTS 4,678,470 A * 7/1987 Nashef et al. ........... 623/23.63
4,774,227 A * 9/1988 Piez et al. ............. 128/DIG. 8
6,206,923 B1 * 3/2001 Boyd et al. .............. 623/16.11
6,299,650 B1 * 10/2001 Van Blitterswijk et al. . 435/372

FOREIGN PATENT DOCUMENTS

WO  WO 95/13767  * 5/1995

* cited by examiner

Primary Examiner—Corrine McDermott
Assistant Examiner—Hieu Phan
(74) Attorney, Agent, or Firm—Sheridan Ross P.C.

(57) ABSTRACT

The composition as described serves for in vivo cartilage repair. It basically consists of a naturally derived osteoinductive and/or chondroinductive mixture of factors (e.g. derived from bone) or of a synthetic mimic of such a mixture combined with a nanosphere delivery system. A preferred mixture of factors is the combination of factors isolated from bone, known as BP and described by Poser and Benedict (WO 95/13767). The nanosphere delivery system consists of nanospheres defined as polymer particles of less than 1000 nm in diameter (whereby the majority of particles preferably ranges between 200–400 nm) in which nanospheres the combination of factors is encapsulated. The nanospheres are loaded with the mixture of factors in a weight ratio of 0.001 to 17% (w/w), preferably of 1 to 4% (w/w) and have a release profile with an initial burst of 10 to 20% of the total load over the first 24 hours and a long time release of at least 0.1 per day during at least seven following days. The nanospheres are composed of e.g. ((D,L)-lactic acid/glycolic acid)-copolymer (PLGA). The loaded nanospheres are e.g. made by phase inversion. The composition is advantageously utilized as a device comprising any biodegradable matrix in which the nanospheres loaded with the factor combination is contained.

20 Claims, 5 Drawing Sheets

COMPOSITION AND DEVICE FOR IN VIVO CARTILAGE REPAIR

BACKGROUND OF THE INVENTION

Articular cartilage, an avascular tissue found at the ends of articulating bones, has no natural capacity to heal. During normal cartilage ontogeny, mesenchymal stem cells condense to form areas of high density and proceed through a series of developmental stages that ends in the mature chondrocyte. The final hyaline cartilage tissue contains only chondrocytes that are surrounded by a matrix composed of type II collagen, sulfated proteoglycans, and additional proteins. The matrix is heterogenous in structure and consists of three morphologically distinct zones: superficial, intermediate, and deep. Zones differ among collagen and proteoglycan distribution, calcification, orientation of collagen fibrils, and the positioning and alignment of chondrocytes (Archer et al., *J. Anat.* 189(1): 23–35, 1996; Morrison et al., *J. Anat.* 189(1): 9–22 1996, Mow et al., *Biomaterials* 13(2): 67–97, 1992). These properties provide the unique mechanical and physical parameters to hyaline cartilage tissue.

In 1965, a demineralized extraction from bovine long bones was found to induce endochondral bone formation in the rat subcutaneous assay (Urist *Science* 150: 893–899, 1965). Seven individual factors, termed Bone Morphogenetic Proteins (BMPs), were isolated to homogeneity and, because of significant sequence homology, classified as members of the TGFβ super-family of proteins (Wozney, et al., *Science* 242: 1528–34, 1988; Wang et al., *Proc. Nat. Acad. Sci.* 87: 2220–2224, 1990). These individual, recombinantly-produced factors also induce ectopic bone formation in the rat model (Luyten et al., *J. Biol. Chem.* 264: 13377–80, 1989; Celeste et al., *Proc. Nat. Acad. Sci.* 87: 9843–50, 1990). In addition, in vitro tests have demonstrated that both BMP-2 and TGFβ-1 induce mesenchymal stem cells to form cartilage (Denker, et al., *Differentiation* 59(1): 25–34, 1995; Denker et al., 41*st Ann. Orthop. Res. Society* 465: 1995). Both BMP-7 and BMP-2 have been shown to enhance matrix production of chondrocytes in vitro (Flechtenmacher *J. Arthritis Rheum.* 39(11): 1896–904, 1996: Sailor et al., *J. Orthop. Res.* 14: 937–945, 1996). From these data we can conclude that not only are the BMPs important regulators of osteogenesis, but that they also play crucial roles during chondrogenic development in vitro.

A partially-purified protein mixture from bovine long bones, termed BP (Bone Protein), also induces cartilage and bone formation in the rat subcutaneous assay (Poser and Benedict, WO95/13767). BP in combination with calcium carbonate promotes bone formation in the body. In vitro, BP induces mesenchymal stem cells to differentiate specifically to the cartilage lineage, in high yields, and to late stages of maturation (Atkinson et al., *J. Cellular Biochem.* 65: 325–339, 1997).

The molecular mechanism for cartilage and bone formation has been partially elucidated. Both BMP and TGFβ molecules bind to cell surface receptors (the BMP/TGFβ receptors), which initiates a cascade of signals to the nucleus that promotes proliferation, differentiation to cartilage, and/or differentiation to bone (Massague *Cell* 85: 947–950, 1996).

In 1984, Urist described a substantially pure, but not recombinant BMP, combined with a biodegradable polylactic acid polymer delivery system for bone repair (U.S. Pat. No. 4,563,489). This system blends together equal quantities of BMP and polylactic acid (PLA) powder (100 μg of each) and decreases the amount of BMP required to promote bone repair.

Hunziker (U.S. Pat. Nos. 5,368,858; 5,206,023) describes a cartilage repair composition consisting of a biodegradable matrix, a proliferation and/or chemotactic agent, and a transforming factor. A two stage approach is used where each component has a specific function over time. First, a specific concentration of proliferation/chemotactic agent fills the defect with repair cells. Secondly, a larger transforming factor concentration transforms repair cells into chondrocytes. Thereby the proliferation agent and the transforming agent may both be TGFβ differing in concentration only. In addition, the patent discloses a liposome encapsulation method for delivering TFGβ-1 serving as transformation agent.

Hattersley et al. (WO 96/39170) disclose a two factor composition for inducing cartilaginous tissue formation using a cartilage formation-inducing protein and a cartilage maintenance inducing protein. Specific recombinant cartilage formation inducing protein(s) are specified as BMP-13, MP-52, and BMP-12, and cartilage maintenance-inducing protein(s) are specified as BMP-9. In one embodiment, BMP-9 is encapsulated in a resorbable polymer system and delivered to coincide with the presence of cartilage formation inducing protein(s).

Laurencin et al., (U.S. Pat. No. 5,629,009) disclose a chondrogenesis-inducing device, consisting of a polyanhydride and polyorthoester, that delivers water soluble proteins derived from demineralized bone matrix, TGFβ, EGF, FGF, or PDGF.

The results of the approaches to cartilage repair as cited above are encouraging but they are not satisfactory. In particular, the repair tissue arrived at is not fully hyaline in appearance and/or it does not contain the proper chondrocyte organization. Furthermore, previous approaches to cartilage repair have been addressed to very small defects and have not been able to solve problems associated with repair of large, clinically relevant defects.

One reason that previous approaches failed to adequately repair cartilage may be that they were not able to recapitulate natural cartilage ontogeny faithfully enough, this natural ontogeny being based on a very complicated system of different factors, factor combinations and factor concentrations with temporal and local gradients. A single recombinant growth factor or two recombinant growth factors may lack the inductive complexity to mimic cartilage development to a sufficient degree and/or the delivery systems used may not have been able to mimic the gradient complexity of the natural system to a satisfactory degree.

Previous approaches may also have failed because growth factor concentrations were not able to be maintained over a sufficient amount of time, which would prevent a full and permanent differentiation of precursor cells to chondrocytes. The loss of growth factor could be caused by diffusion, degradation, or by cellular internalization that bypasses the BMP/TGFβ receptors. Maintaining a sufficient growth factor concentration becomes particularly important in repair of large sized defects that may take several days or several weeks to fully repopulate with cells.

The object of this invention is to create a composition for improved cartilage repair in vivo. The inventive composition is to enable in vivo formation of repair cartilage tissue which tissue resembles endogenous cartilage (in the case of articular cartilage with its specific chondrocyte spatial organization and superficial, intermediate, and deep cartilage zones) more closely than repair tissue achieved using known compositions for inducing cartilage repair. A further object of the invention is to create a device for cartilage repair which device contains the inventive composition.

This object is achieved by the composition and the device as defined by the claims.

BRIEF DESCRIPTION OF THE INVENTION

The inventive composition basically consists of a naturally derived osteoinductive and/or chondroinductive mixture of factors (e.g. derived from bone) or of a synthetic mimic of such a mixture combined with a nanosphere delivery system. A preferred mixture of factors is the combination of factors isolated from bone, known as BP and described by Poser and Benedict (WO 95/13767). The nanosphere delivery system consists of nanospheres defined as polymer particles of less than 1000 nm in diameter (whereby the majority of particles preferably ranges between 200–400 nm) in which nanospheres the combination of factors is encapsulated. The nanospheres are loaded with the mixture of factors in a weight ratio of 0.001 to 17% (w/w), preferably of 1 to 4% (w/w) and have an analytically defined release profile (see description regarding FIG. 2) showing an initial burst of 10 to 20% of the total load over the first 24 hours and a long time release of at least 0.1 per day during at least seven following days, preferably of 0.1 to 1% over the following 40 to 60 days. The nanospheres are composed of e.g. (lactic acid-glycolic acid)-copolymers (Poly-(D,L)lactic acid-glycolic acid) made of 20 to 80% lactic acid and 80 to 20% of glycolic acid, more preferably of 50% lactic acid and 50% of glycolic acid.

The loaded nanospheres are e.g. made by phase inversion according to Mathiowitz et al. (*Nature*, 386: 410–413, 1997) or by other methods known to those skilled in the art (Landry, Ph.D Thesis, Frankfurt, Germany).

The inventive composition is advantageously utilized as a device comprising any biodegradable matrix including collagen type I and II, and hyaluronic acid in which matrix the nanospheres loaded with the factor combination is contained. The matrix can be in the form of a sponge, membrane, film or gel. The matrix should be easily digestible by migrating cells, should be of a porous nature to enhance cell migration, and/or should be able to completely fill the defect area without any gaps.

It is surprisingly found that the inventive composition consisting of an osteoinductive and/or chondroinductive combination of factors (e.g. derived from natural tissue) encapsulated in nanospheres as specified above, if applied to a defect area of an articular cartilage, leads to the transformation of virtually all precursor cells recruited to the repair area to chondrocytes, and furthermore, leads to a homogenous chondrocyte population of the repair area and to a chondrocyte order and anisotropic appearance as observed in endogenous hyaline cartilage. These findings encourage the prospect that the inventive composition may lead to significant improvements also regarding repair of large defects.

As mentioned above, instead of an osteoinductive and/or chondroinductive mixture of factors derived from bone (BP), the inventive composition may comprise natural factor mixtures derived from other tissues (e.g. cartilage, tendon, meniscus or ligament) or may even be a synthetic mimic of such a mixture having an osteoinductive and/or chondroinductive effect. Effective mixtures isolated from natural tissue seem to contain a combination of proliferation, differentiation, and spatial organizing proteins which in combination enhance the tissue rebuilding capacity more effectively than single proteins (e.g. recombinant proteins).

The specified, analytically defined release profile of such factor mixtures from nanospheres results in the formation of concentration gradients of proliferation and differentiation factors, which obviously mimics the complex gradients of factors observed during natural development very well. The nanosphere extended release profile is sufficient to provide growth factor during the time frame that repair cells arrive into the matrix. The release profile obviously leads to a homogenous population of a matrix with precursor cells, to full differentiation of virtually all of the precursor cells to chondrocytes, and to the formation of an endogenous hyaline cartilage structure.

Another advantage of the inventive composition is that when the nanospheres are placed in a matrix to form a device for cartilage repair, they are randomly distributed and remain in place when in a joint cartilage defect. During cellular infiltration and differentiation, the nanospheres are in the correct position over the correct time frame.

Nanospheres have been demonstrated to adhere to the gastrointestinal mucus and cellular linings after oral ingestion (Mathiowitz et al., *Nature*, 386 410–413 1997). We envisage that nanospheres also adhere to cartilage precursor cells and furthermore, may also adhere to BMP/TGFβ receptors located on the cell membrane. This property allows localized high-efficiency delivery to the target cells and/or receptors. Because of the nanosphere small size and the chemical properties, they are more effective than liposomes or diffusion controlled delivery systems. The efficient delivery to the receptors will facilitate chondrogenesis.

Derived from the above findings, we envisage the following mechanism for cartilage repair using the effect of the inventive composition. During the first 24 hours (initial burst) 10 to 20% of the total load of the factor mixture is released from the nanospheres into the matrix and diffuses into the synovial environment. Following the initial burst, the nanospheres begin to release factors at a slow rate, which produces gradients of proliferation, differentiation, and spatial organizing proteins. In response to such gradients, precursor cells migrate to the defect site. The loaded nanospheres adhere to cartilage precursor cells and to the BMP and TGFβ receptors to provide localized highly efficient delivery. The precursor cells become differentiated to chondrocytes and secrete type II collagen and cartilage-specific proteoglycans. The composition of the present invention stimulates differentiation of virtually all of these cells to overt chondrocytes and induces an ordered cartilage structure which closely resembles hyaline cartilage. Furthermore, we envisage that this release system will allow homogenous repair of large defect sites and repair of defects from patients with low quantities of precursor cells.

For in vivo cartilage repair, the inventive device consisting of a matrix and the loaded nanospheres is placed in a chondral lesion that was caused by trauma, arthritis, congenital, or other origin. The damage can result in holes or crevices or can consist of soft, dying, or sick cartilage tissue that is removed surgically prior to implantation of the device. Because of the unique properties of the inventive device precursor cells populate the matrix, differentiate to chondrocytes, and form hyaline cartilage.

Application of the inventive composition (without matrix) e.g. by injection can be envisaged also, in particular in the case of small defects. Thereby at least 2 µg of the composition per ml of defect size is applied or at least 20 ng of the osteoinductive and/or chondroinductive mixture encapsulated in the nanospheres is applied per ml defect size.

The inventive composition and the inventive device are suitable for repair of cartilage tissue in general, in particular for articular cartilage and for meniscus cartilage.

BRIEF DESCRIPTION OF THE FIGURES

The following figures illustrate the physical and chemical parameters of the inventive composition, the in vitro cartilage inductive activity of BP released from nanospheres and in vivo repair of an articular cartilage defect using the inventive device.

DETAILED DESCRIPTION OF THE INVENTION

Figure 1:
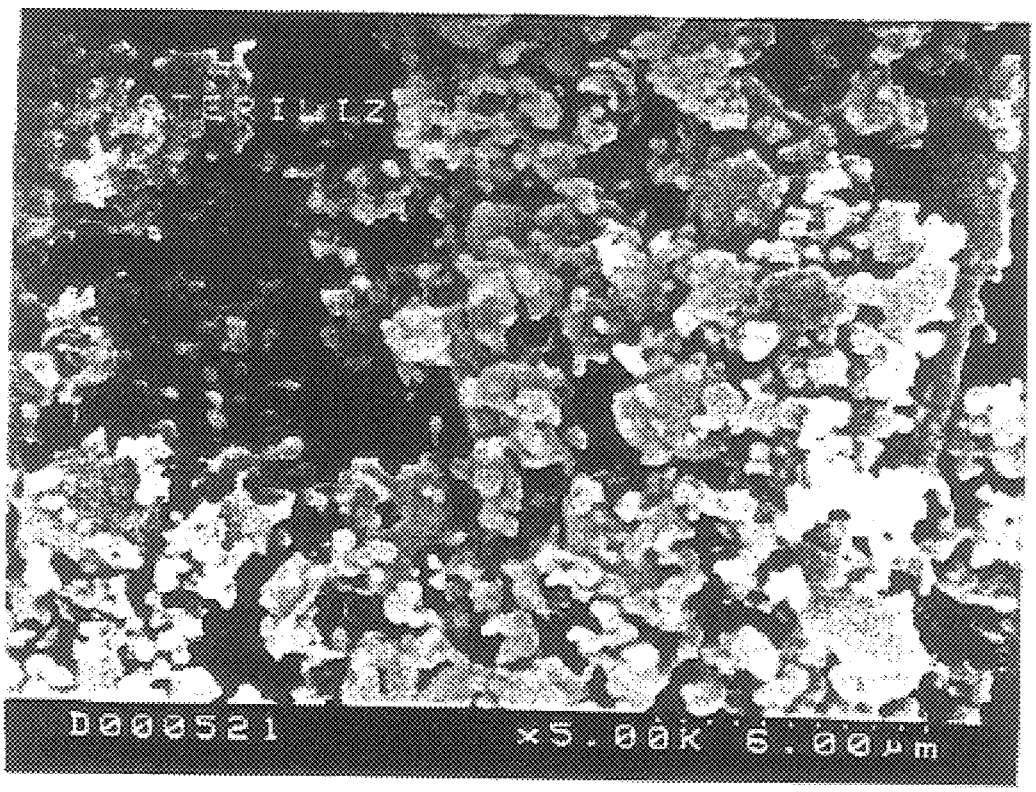
FIG. 1 shows a scanning electron micrograph of BP-loaded nanospheres.

FIG. 1 shows a scanning electron micrograph of BP-loaded nanospheres. The microparticle sizes range from 100–1000 nm with the majority of individual particles ranging between 200–400 nm.

The release rate profile of the inventive composition was determined by in vitro analysis of BP delivered from nanospheres. These nanospheres were made by phase inversion according to the method as disclosed by Mathiowitz et al. (Nature 386, 410–414, 1997) of ((DL)lactic acid/glycolic acid)-copolymer containing the two acids in a weight ratio of 50:50 and they were loaded with 1% and with 4% of BP.

Figure 2:
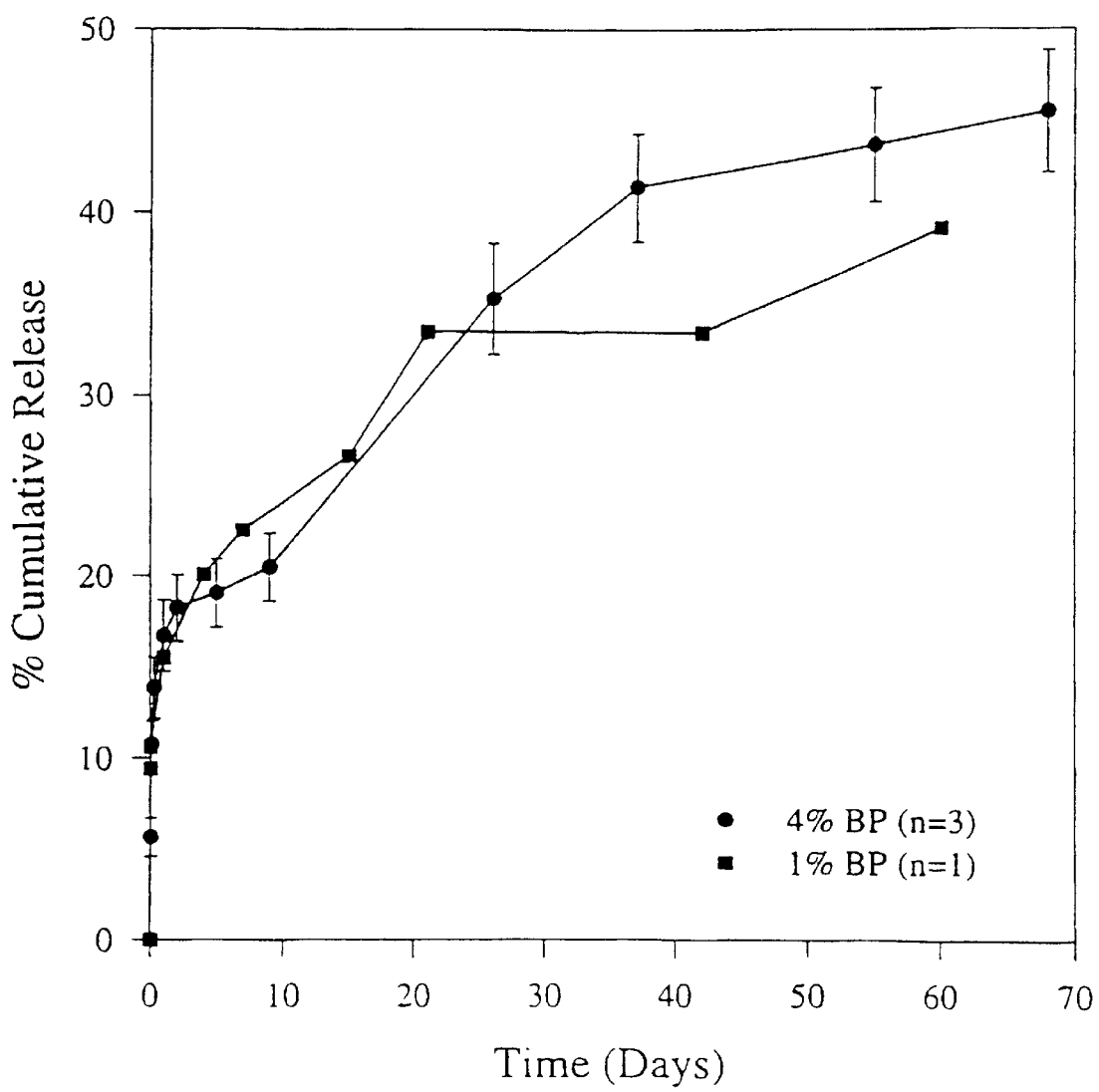
FIG. 2 shows the release profile (cumulative release vs. time) of the inventive composition.

For determination of the release rate profile, the nanospheres were placed in a sterile saline solution and incubated at 37° C. BP released into the supernatant was measured using a BCA assay (Pierce). BP released from the nanospheres as specified shows two successive and distinct profile parts: a fast release (initial burst) of approximately 10 to 20% of the loaded BP over the first 24 hours and a slow release of 0.1 to 1% per day (cumulative 40% to 50%) over 40 to 60 days (FIG. 2).

The release is intermediate between zero-order and first-order kinetics. Both the 1% and 4% encapsulated BP have similar release profiles.

For attaining release rate profiles as specified above and as necessary for the improved results in cartilage repair the nanospheres are to be adapted accordingly when using factor mixtures other than BP. Thereby, e.g the composition of the nanosphere copolymer, the molecular weight of the polymer molecules and/or the loading percentage of the nanospheres may be changed. The optimum nanosphere character for each specific case has to be found experimentally whereby the release rate profile is analyzed in vitro as described above.

In the same way, the nanosphere delivery system can be modified regarding the percentage of BP to be released in the first 24 hours, percentage of BP to be released after 24 hours and/or length of time after the first 24 hours during which the remainder of BP is released. In addition, the percentage of BP loaded to the nanospheres is of course variable too, whereby for obtaining the results as described for the specified composition, all the modifications are to be chosen such that the resulting delivery keeps within the range as specified.

All of the above parameters can be modified to account for the patient's age, sex, diet, defect location, amount of blood present in the defect, and other clinical factors to provide optimal cartilage repair. For example, nanospheres with longer release rates are used for treating larger defects and/or for patients with fewer precursor cells (e.g. older patients or patients with degenerative symptoms). In contrast, patients with larger quantities of progenitor cells and/or smaller defects may require a shorter release rate profile.

Figure 3:
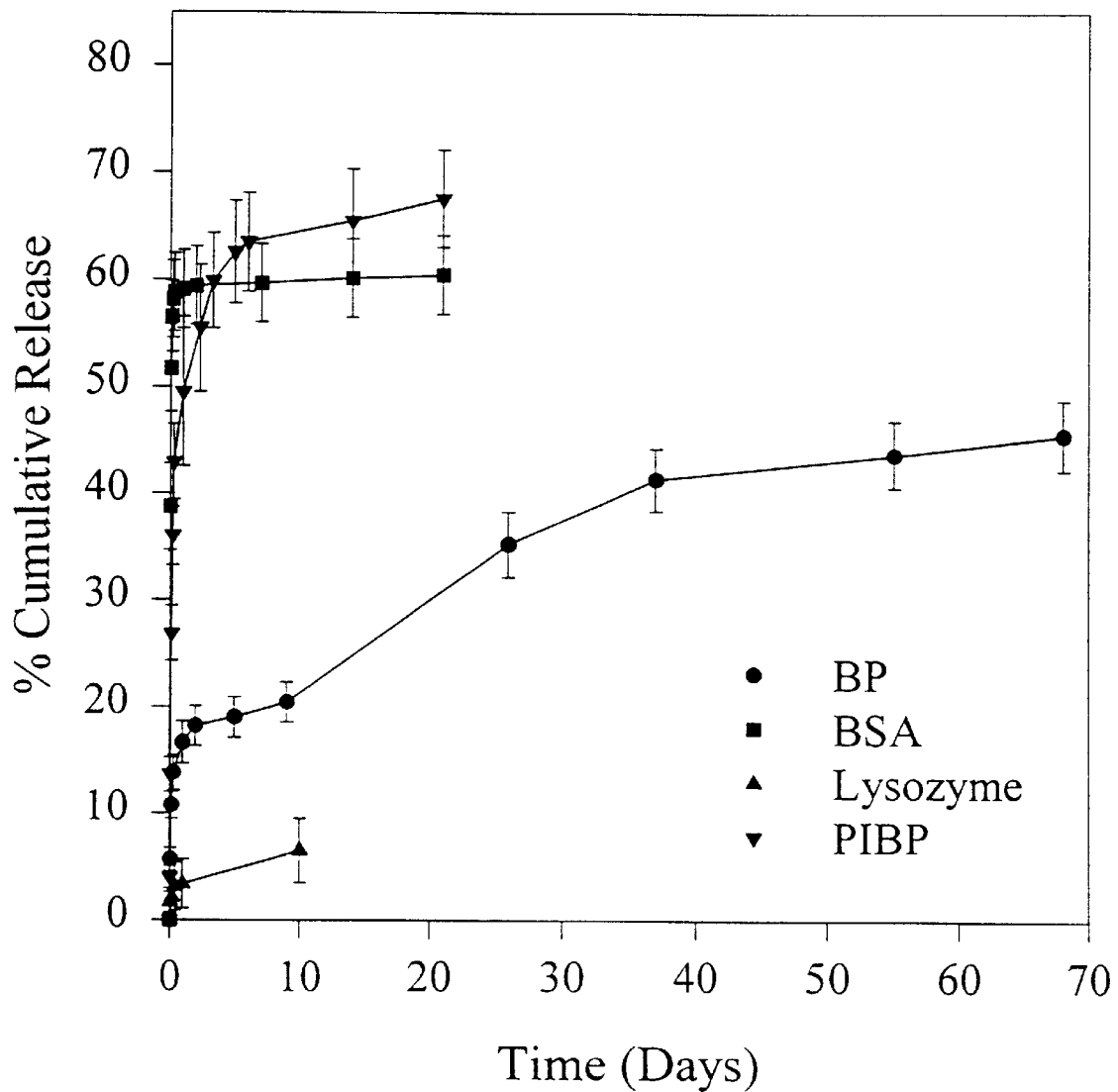
FIG. 3 shows the release profile of the inventive composition compared with release profiles of nanosphere delivery systems loaded with other proteins.

FIG. 3 shows the release profile as shown in FIG. 2 for nanospheres as specified above loaded with BP and with other proteins (same loading percentages) such as BSA (bovine serum albumin) or lysozyme. The drastically different release characteristics shows that the profile is dependent on the protein type also. The same is valid for a more hydrophobic mixture of bovine bone derived proteins (PIBP).

FIG. 3 illustrates the singularity of the inventive combination consisting of the specific delivery system (nanospheres as specified above encapsulating the factors) and the specific protein mixture (BP) which is obviously the key to the improved results in cartilage repair as observed when using the inventive composition or device.

Figure 4:
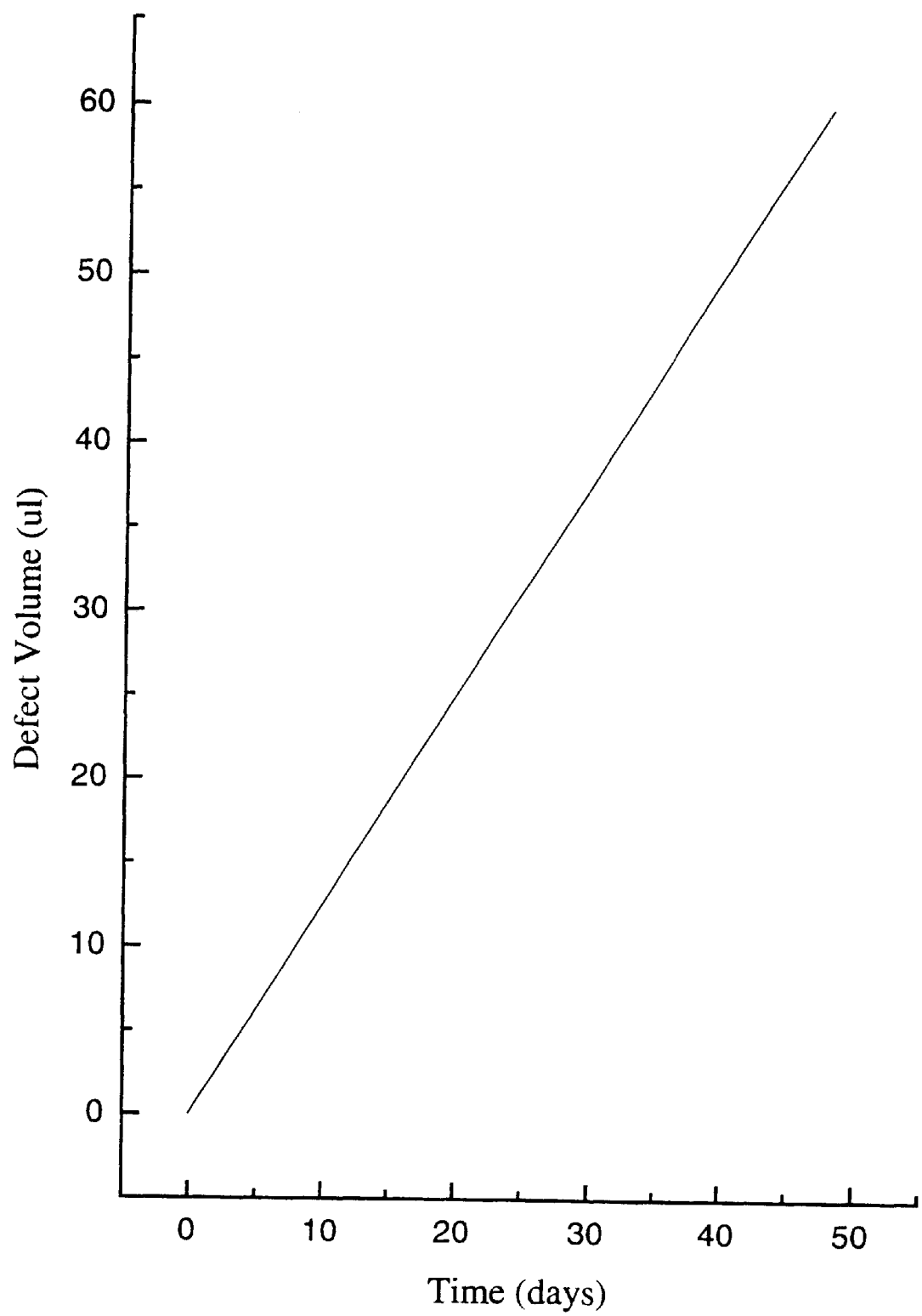
FIG. 4 shows the volume of a cartilage defect vs. the days required for populating the defect with repair cells.

To determine the length of time required for precursor cell repopulation of different sized defects, the following calculation was performed. We estimate that approximately 50,000 cells are recruited to the defect/day. Since the cellular density of cartilage is about $4 \times 10^7$ cells/ml, a 10 µl volume defect will take approximately 8 days to fill with cells. FIG. 4 plots the number of days required to fill different volume defects with cells. The Figure assumes an infinite supply of cells and a constant rate of cell attraction to the defect site. The graph demonstrates that the larger a defect size is, the more time is required to completely fill it with cells. Since a 60 µl volume defect will take over 45 days to fill, this Figure demonstrates the necessity for a long term release of factors to induce differentiation of the precursor cells over up to a two month period.

To determine whether BP bioactivity is harmed by the encapsulation process and to determine whether the released BP was fully bioactive, the following assay was performed. Previously, it was demonstrated that 10T1/2 micromass cultures exposed to BP induce formation of a three dimensional spheroid structure that can be observed macroscopically in tissue culture wells (Atkinson et al., *J. Cellular Biochem.* 65: 325–339, 1997). BP concentrations equal or greater than 20 ng/ml were required for spheroid formation. No spheroid forms in the absence of BP or at concentrations less than 10 ng/ml (see following table). In this assay, 10T1/2 mesenchymal stem cells act as in vitro models for the precursor cells recruited to a natural defect.

We employed the same assay to test the bioactivity of BP released from 1% loaded nanospheres. BP was eluted from nanospheres at 37° C. in a 5% $CO_2$ humidified incubator. After 24 hours 16% BP is released; and between 24 hours and 7 days, 7% BP was released (FIG. 2). The supernatant was collected, serial dilutions were made, and the supernatant was added to 10T1/2 micromass cultures. BP released from nanospheres at both time points formed spheroids at concentrations greater than 20 ng/ml, but not at concentrations between 0 and 10 ng/ml (see following table). Non-encapsulated BP also formed spheroids at concentrations greater than 20 ng/ml, but not at concentrations between 0 and 10 ng/ml. We conclude that both nanosphere encapsulation and release of BP does not inhibit BP bioactivity.
Spheroid Formation (−=No Spheroid Formation;+=Spheroid Formation)

| state of used BP | BP concentration (ng/ml) | |
|---|---|---|
| | 0–10 | 20–1000 |
| non-encapsulated BP | − | + |
| releaeed from nanospheres (24 h) | − | + |
| released from nanospheres (168 h) | − | + |

Figure 5:
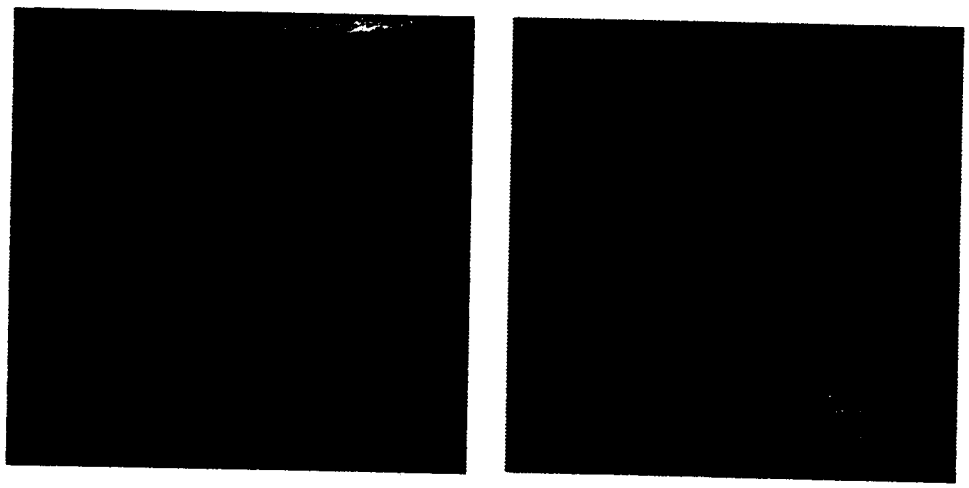
FIG. 5 shows micromass cultures in the presence or absence of nanospheres loaded with BP.

To determine the effect of BP slow release in the direct presence of micromass cultures, the following assay was performed. Nanospheres were washed for 24 hours and the supernatant was discarded. The nanospheres were then added to micromass cultures at a quantity such that 10 or 25 ng/ml of BP would be released over 24 hours. Release of 25 ng/ml resulted in spheroid formation whereas release of 10 ng/ml did not form spheroids (FIG. 5). Similarly, the addition of 10 ng of non-encapsulated BP per ml did not form a spheroid whereas the addition of 25 ng of non-encapsulated BP per ml did form a spheroid. Regarding the specific in vitro set-up, we conclude that slow release of BP over 24 hours is as effective as a single dose of BP.

To determine whether the BP released from nanospheres was as chondrogenic as non-encapsulated BP, spheroids were analyzed for type II collagen and proteoglycan content. 10T1/2 spheroids from the above assay that had formed with 1 µg of released BP per ml or 1 µg of non-encapsulated BP per ml were tested histologically with Azure and H+E stains and immunocytochemically with antibodies to type II collagen after 7 days. Both encapsulated and non-encapsulated BP induced cartilage markers such as type II collagen, proteoglycan, and round cell shape. In addition, no qualitative differences were observed between encapsulated and non-encapsulated BP with respect to cell quantity, viability, morphology, or organization. We conclude that BP retains full chondrogenic capacity after release from nanospheres.

The in vitro models used for determining the chondroinductive effect of BP differ from the in vivo case by the fact that in the in vitro case the precursor cells are present in an appropriate number and in an appropriate distribution whereas in the in vivo case the precursor cells first have to populate the defect and for this reason have to migrate into the defect. Only in the latter case and for achieving repair cartilage which resembles natural cartilage to a high degree, it is essential for the BP to be released over a prolonged time period according to a specific release profile.

EXAMPLE

The following example shows that BP released from nanospheres induces cartilage repair in chondral defects in vivo whereby virtually all cells recruited to the defect become chondrocytes, whereby the cell structure obtained is ordered, and whereby a hyaline matrix is built up.

Using a sheep model, unilateral defects of 0.5 mm width, 0.5 mm depth and 8 to 10 mm length were created in the trochlear groove of the patella. The defects did not penetrate the subchondral bone. The sheep employed in this study were seven years old and displayed degenerative symptoms, including brittle bones, chondromalacia, and subchondral cysts. Because of their advanced age and degenerative symptoms, these amimals probably have decreased numbers of precursor cells. The defects were then dressed according to Hunziker and Rosenberg (J. Bone Joint Surg. 78A(5): 721–733, 1996) with minor changes. Briefly, after enzymatic proteoglycan removal with Chondroitinase AC, 2.5 µl of a solution containig 200 units Thrombin per ml was placed in the defect. Then, a paste was filled into the defect, the paste containing per ml: 60 mg Sheep Fibrinogen (Sigma), 88 mg Gelfoam (Upjohn) and either 10 µg of BP-nanospheres or 10 µg of BP-nanospheres plus 80 ng rhIGF-1 (R+D Systems).

The nanospheres used were the nanospheres as specified in the description regarding FIG. 2 and they were loaded with 1% (w/w) of BP.

Assuming that the in vitro determined release rate is approximately the same as for the in vivo case, 10 to 20 ng BP per ml were released during the first 24 hours and approximately 0.1 to 1 ng per day for the following approximately 60 days.

After eight weeks, necropsies were performed. The repaired cartilage histology showed that virtually all of the precursor cells were differentiated to chondrocytes throughout the defect. In addition, there was an ordered cartilage appearance with cells on the top being more flattened morphologically than cells in the center and with the presence of ordered, stacked chondrocytes in the lowest zone. The repaired cartilage was fully integrated into the endogenous tissue. In addition, the cartilage repaired with only BP-nanospheres was not significantly different from the cartilage repaired using BP-nanospheres plus IGF-1.

In conclusion, these results demonstrate that BP released from nanospheres is sufficient for cartilage repair and that no additintional factor is required (such as e.g recombinant factor IGF-1). Using the inventive device constitutes a one step method for cartilage repair, whereby the nanosphere release of BP is sufficient for differentiation of virtually all of the precursor cells to chondrocytes and for induction of an ordered cartilage structure.

OTHER PUBLICATIONS

Archer C W, Morrison E H, Bayliss M T, Ferguson M W: The development of articular cartilage: II. The spatial and temporal patterns of glycosaminoglycans and small leucine-rich proteoglycans; J Anat (ENGLAND) 189 (Pt 1): 23–35 (1996)

Atkinson B L, Fantle, K S, Benedict J J, Huffer W E, Gutierrez-Hartmann A: A Combination of Osteoinductive Bone Proteins Differentiates Mesenchymal C3H/10T1/2 Cells Specifically to the Cartilage Lineage; J. Cellular Biochem. 65: 325–339 (1997).

Celeste A J, Iannazzi J A, Taylor R C, Hewick R M, Rosen V, Wang E A, Wozney J M: Identification of transforming growth factor beta family members present in bone-inductive protein purified from bovine bone; Proc Natl Acad Sci USA, December 87(24): 9843–7 (1990)

Denker A E, Nicoll S B, Tuan R S: Formation of cartilage-like spheroids by micromass cultures of murine C3H10T1/2 cells upon treatment with transforming growth factor β1'; Differentiation 59(1): 25–34 (1995)

Denker A E, Nicoll S B, Tuan R S: 41st Annual Meeting Orthop. Res. Society.(abstract): 465 (1995)

Flechtenmacher J, Huch K, Thonar E J, Mollenhauer J A, Davies S R, Schmid T M, Puhl W, Sampath T K, Aydelotte M B, Kuettner K E: Recombinant human osteogenic protein 1 is a potent stimulator of the synthesis of cartilage proteoglycans and collagens by human articular chondrocytes; Arthritis Rheum, November 39(11): 1896–904 (1996)

Hunziker E B and Rosenberg L C: Repair of Partial-Thickness Defects in Articular Cartilage: Cell Recruitment from the Synovial Membrane; J. Bone Joint Surgery 78-A(5): 721–733 (1996)

Kim S, Turker M S, Chi E Y, Sela S, Martin G M: Preparation of multivesicular liposomes; Bioch. et Biophys. Acta 728:339–348 (1983)

Landry F B: Degradation of Poly (D,L-lactic acid) Nanoparticles in artificial gastric and intestinal fluids; in vivo uptake of the nanoparticles and their degradation products; Thesis for the Dept. of Biochemistry, Pharmacy, and Food Chemistry of the Johann Wolfgang Goethe University in Frankfurt, Germany Luyten F P, Cunningham N S, Ma S, Muthukumaran N, Hammonds R G, Nevins W B, Woods W I, Reddi A H: Purification and partial amino acid sequence of osteogenin, a protein initiating bone differentiation; J Biol Chem, 264(23): 13377–80 (1989)

Massague J: TGFβ Signaling: Receptors, Transducer, and Mad Proteins; Cell 85: 947–950 (1996)

Mathiowitz E, Jacob J S, Jong Y S, Carino G P, Chickering D E, Chaturvedi P, Santos C A, Vijayaraghavan K, Montgomery S, Bassett M, Morrell C: Biologically erodable microspheres as potential oral drug delivery systems; Nature 386: 410–4 (1997)

Morrison E H, Ferguson M W, Bayliss M T, Archer C W: The development of articular cartilage: I. The spatial and temporal patterns of collagen types; J Anat (ENGLAND) 189(Pt 1): 9–22 (1996)

Mow V C, Ratcliff A, Poole A R: Cartilage and diarthrodial joints as paradigms for hierarchical materials and stuctures; Biomaterials 13(2): 67–97 (1992)

Sailor L Z, Hewick R M, Morris E A: Recombinant human bone morphogenetic Protein-2 maintains the articular chondrocyte phenotype in long-term culture; J. Orthop. Res. 14: 937–945 (1996)

Urist M R: Bone: formation by autoinduction; Science 150: 893–899 (1965)

Wang E A, Rosen V, D'Alessandro J S, Bauduy M, Cordes P, Harada T, Israel D I, Hewick R M, Kerns K M, LaPan P, Luxenberg D P, McQuaid D, Moutsatsos I, Nove J, Wozney J M: Recombinant human bone morphogenetic protein induces bone formation;' Proc Natl Acad Sci USA, 87(6): 2220–4 (1990)

Wozney J M, Rosen V, Celeste A J, Mitsock L M, Whitters M J, Kriz R W, Hewick R M, Wang E A: Novel Regulators of bone formation: molecular clones and activities; Science 242: 1528–34 (1988)

What is claimed is:

1. Composition for inducing in vivo cartilage repair comprising an osteoinductive and/or chondroinductive protein mixture derived from bone, cartilage, tendon, meniscus or ligament or a sythetic mimic of such a mixture encapsulated in nanospheres, wherein the nanospheres are polymer particles having a size of less than 1000 nm and an in vitro analytically determined profile of release into saline solution with an initial burst of 10 to 20% of the total load over the first 24 hours and a long time release of 0.1 and 1% per day during 40 to 70 days and wherein the nanospheres are loaded with an amount of the mixture constituting between 0.001 and 17% of the total weight of the loaded nanospheres.

2. Composition according to claim 1, characterized in that the osteoinductive and/or chondroinductive protein mixture is the mixture known as BP (bone protein) derived from demineralized bovine long bones and partly purified.

3. Composition according to claim 2, characterized, in that the nanospheres are loaded with between 1 and 4% weight percent of BP.

4. Composition according to claim 1, characterized in that the nanospheres consist of ((D,L)lactic acid/glycolic acid)-copolymer containing 20 to 80% of lactic acid and 80 to 20% of glycolic acid.

5. Composition according to claim 1, characterized in that the ((D,L)lactic acid/glycolic acid)-copolymer contains 50% of lactic acid and 50% of glycolic acid.

6. Composition according to claim 1, characterized in that the nanospheres are made by phase inversion.

7. Device containing the composition according to claim 1 and further comprising a porous biodegradable matrix suitable to be placed in a cartialge defect.

8. Device according to claim 7, characterized in that it contains at least 2 µg of loaded nanospheres per ml of the porous biodegradable matrix.

9. Device according to claim 7, characterized in that it contains at least 20 ng of the osteoinductive and/or chondroinductive protein mixture per ml of the porous biodegradable matrix.

10. Device according to claim 7, characterized in that the porous biodegradable matrix has the form of a sponge, membrane, film or gel.

11. Device according to claim 7, characterized in that the porous biodegradable matrix consists of collagen type I, collagen type II or hyaluronic acid.

12. A method of cartilage repair in an animal with a degenerative disease comprising placing the device of claim 7 in a defect area of cartilage of said animal.

13. Method for in vivo cartilage repair comprising the step of placing a a device according to claim 7 into a cartilage defect.

14. Method according to claim 13, characterized in that the defect is dressed before the step of placing.

15. A method of in vivo cartilage repair in an animal comprising applying the composition of claim 1 to said animal wherein application of said composition results in the formation of an endogenous hyaline cartilage structure.

16. A method of cartilage repair in an animal with a degenerative disease comprising applying the composition of claim 1 to a defect area of cartilage of said animal.

17. Method for in vivo cartilage repair of a defect comprising the step of administering to the cartilage defect a composition according to claim 1.

18. Method according to claim 17, characterized in that the composition is administered by injection.

19. Method according to claim 17, characterized in that the composition is administered in an amount of at least 2 µg per ml defect size.

20. Method according to claim 17, characterized in that the composition is administered in an amount such that the osteoinductive and/or chondroinductive protein mixture is present in the defect in an amount of at least 20 ng per ml defect size.

* * * * *